(12) United States Patent
Hua et al.

(10) Patent No.: US 12,364,436 B2
(45) Date of Patent: Jul. 22, 2025

(54) AUTOMATIC TEST DEVICE AND METHOD FOR AUDITORY BRAINSTEM RESPONSE

(71) Applicant: Shanghai Ninth People's Hospital Affiliated to Shanghai Jiaotong University School of Medicine, Shanghai (CN)

(72) Inventors: Yunfeng Hua, Shanghai (CN); Hao Wu, Shanghai (CN); Haoyu Wang, Shanghai (CN); Bei Li, Shanghai (CN); Xu Ding, Shanghai (CN); Zhiwu Huang, Shanghai (CN); Xueling Wang, Shanghai (CN)

(73) Assignee: Shanghai Ninth People's Hospital Affiliated to Shanghai Jiaotong University School of Medicine, Shanghai (CN)

( * ) Notice: Subject to any disclaimer, the term of this patent is extended or adjusted under 35 U.S.C. 154(b) by 934 days.

(21) Appl. No.: 17/605,306

(22) PCT Filed: Sep. 17, 2019

(86) PCT No.: PCT/CN2019/106154
§ 371 (c)(1),
(2) Date: Oct. 21, 2021

(87) PCT Pub. No.: WO2020/220564
PCT Pub. Date: Nov. 5, 2020

(65) Prior Publication Data
US 2022/0183631 A1 Jun. 16, 2022

(30) Foreign Application Priority Data
Apr. 30, 2019 (CN) .......................... 201910362550.0

(51) Int. Cl.
*A61B 5/00* (2006.01)
*A61B 5/12* (2006.01)
*A61B 5/38* (2021.01)

(52) U.S. Cl.
CPC ............ *A61B 5/7203* (2013.01); *A61B 5/121* (2013.01); *A61B 5/38* (2021.01); *A61B 5/7235* (2013.01)

(58) Field of Classification Search
CPC ......... A61B 5/7203; A61B 5/38; A61B 5/121; A61B 5/7235
(Continued)

(56) References Cited

U.S. PATENT DOCUMENTS 5,697,379 A    12/1997  Neely et al.
6,071,246 A *  6/2000  Sturzebecher ........... A61B 5/12
                                                      600/559
(Continued)

FOREIGN PATENT DOCUMENTS

CN    1799496 A      7/2006
CN    101516263 A    8/2009
(Continued)

OTHER PUBLICATIONS

China National Intellectual Property Administration, "Search Report," issued in Chinese Patent Application No. 201910362550.0, which is a counterpart to U.S. Appl. No. 17/605,306, 4 pages (1 page of English Translation and 3 pages of Search Report).
(Continued)

*Primary Examiner* — Mark Edwards
(74) *Attorney, Agent, or Firm* — Amster, Rothstein & Ebenstein LLP

(57) ABSTRACT

An automatic test device and method for auditory brainstem response (ABR) collects an ABR dataset at a plurality of sound loudness levels, increases the times of level averaging
(Continued)

by iteration based on an adaptive average method, and improves a signal-to-noise ratio until ABR signal detection conditions are met. Signal detection includes determining that the time lag between average curves obtained from the ABR dataset is within a specified range. Iteration is terminated when the ABR signal is detected or a maximum number of iterations is reached. A minimum loudness level required to detect the ABR signal is used as a hearing threshold. An accurate loudness level corresponding to the hearing threshold is obtained by function fitting on the number of iterations used at each loudness level and interpolation. The threshold detection can effectively reduce the number of times that an ABR recording needs to be acquired.

11 Claims, 9 Drawing Sheets

(58) Field of Classification Search
USPC .......................................................... 600/545
See application file for complete search history.

(56) References Cited

U.S. PATENT DOCUMENTS

| | | | |
|---|---|---|---|
| 6,196,977 | B1 | 3/2001 | Sininger et al. |
| 6,200,273 | B1 | 3/2001 | Sininger et al. |
| 2003/0187638 | A1* | 10/2003 | Causevic ............ G10L 21/0208 704/226 |
| 2010/0076338 | A1 | 3/2010 | Kwak |
| 2012/0197153 | A1 | 8/2012 | Kraus et al. |

FOREIGN PATENT DOCUMENTS

| | | |
|---|---|---|
| CN | 106725515 A | 5/2017 |
| CN | 109998539 A | 7/2019 |

OTHER PUBLICATIONS

IInternational Search Report received for PCT Patent Application No. PCT/CN2019/106154, mailed on Feb. 3, 2020 (2 pages of English Translation of International Search Report and 5 pages of original International Search Report).

* cited by examiner

AUTOMATIC TEST DEVICE AND METHOD FOR AUDITORY BRAINSTEM RESPONSE

CROSS-REFERENCE TO RELATED APPLICATIONS

This application is a U.S. national stage entry under 35 U.S.C. § 371 of PCT International Patent Application No. PCT/CN2019/106154, filed Sep. 17, 2019, which claims priority to Chinese Patent Application No. CN 201910362550.0, filed Apr. 30, 2019, the contents of each of which are incorporated herein by reference in their entirety.

FIELD OF TECHNOLOGY

The present invention relates to data processing technology, in particular to an automatic test device and method for auditory brainstem response.

BACKGROUND

Auditory Brainstem Response (ABR) is an electroencephalogram (EEG) change induced by sound stimulation, its characteristic waveform occurs within 10 milliseconds after stimulation, and can be recorded by electrodes placed on human or animal heads. The non-invasive nature of ABR has led to its widespread clinical use as a means of hearing test, especially in infants and young children, people with intellectual disabilities, and intraoperative patients, whose hearing assessment cannot be accomplished through verbal communication or physical movements. In clinical practice, the hearing threshold (the minimum loudness level used that can induce the characteristic waveform of the subject's ABR) has become one of the most important indicators for the evaluation of hearing function.

However, because a signal-to-noise ratio of ABR dataset varies widely and the waveform varies greatly at different sound loudness level, they are now basically judged by a specialist based on recordings averaged over hundreds of times. As the determination of threshold sound level relies on subjective judgment, the accuracy of the results highly depends on personal experience and skills, and increases the demand on professional manpower, which cannot meet the increasing clinical needs, as well as causes great difficulties for the nationwide hearing screening of infants and young children. Varying signal-to-noise ratio and waveform also makes it difficult to automate the ABR data analysis. Over the past three to four decades, a series of efforts have been made to automate ABR-based hearing tests, and several solutions have been proposed, but no mature and reliable commercial products have been released.

SUMMARY

The present invention provides an automatic test device and method for auditory brainstem response (ABR), which can automatically process and analyze data from an ABR test efficiently and reliably based on an adaptive average method.

To achieve the above purpose, a technical solution of the present invention is providing an automatic routine for ABR test, which comprises:

A1, acquiring corresponding ABR data at an initial sound loudness level;
A2, gradually increasing, based on an operation of an adaptive level averaging method, the times of level averaging through iteration until conditions of an ABR signal detection are met; the conditions of the ABR signal detection including: after grouping ABR recordings upon a current loudness level in a current iteration, respectively calculating an average response curve of each group according to current average times, obtaining a time lag where a maximum value of cross-correlation function between the groups is located, and judging whether an ABR signal with time-locked characteristics exists based on the rule that whether a deviation of the time lag is within a specified range;
A3, judging whether the ABR signal is detected in step A2: if the ABR signal is detected, executing step A4; if the ABR signal is not detected, executing step A5;
A4, judging whether the current loudness level reaches a set minimum; if the minimum loudness level is not reached, acquiring the ABR dataset at an updated loudness level and combining with recorded datasets, re-executing step A2, the updated loudness level being obtained by subtracting a set step size from the current loudness level; if the minimum loudness level is reached, executing step A6;
A5, judging whether the ABR signal is not detected at successive P loudness levels: if the ABR signal is not detected for the successive P loudness levels, executing step A6; otherwise, jumping to step A4;
A6, using the minimum loudness level required for detecting the ABR signal as hearing threshold; or in the routines of the adaptive average method, obtaining the loudness level corresponding to the hearing threshold by function fitting and interpolation on the number of executed iterations at each loudness level from the initial to the minimum loudness level.

Alternatively, in step A2, the operation of the adaptive average method comprises:

in step A2, the operation of the adaptive average method comprises:
S1', dividing the ABR recordings that are time curves of which an input type is repeated single recording into two groups randomly and respectively calculating an average curve;
S2', calculating the cross-correlation function of the two groups after being averaged respectively;
S3', obtaining the time lag where the maximum value of the cross-correlation coefficient is located;
S4', comparing an absolute value of the obtained time lag with a value of k to judge whether a deviation of the time lag is within k data points:
if the absolute value of the time lag is less than the value of k, indicating that the deviation of the time lag is within the k data points, which denotes that a stable time-locked signal is detected, then stopping data acquisition, which corresponds to a case that the ABR signal is detected;
if the absolute value of the time lag is not less than the value of k, indicating that the deviation of the time lag is not within the k data points, which denotes that no stable time-locked signal is detected, then proceeding to step S5';
S5', judging whether a maximum number of iterations at the current loudness level is reached;
if the maximum number of iterations is reached, stopping data acquisition, which corresponds to a case that no ABR signal is detected; if the maximum number of iterations is not reached, further adding newly acquired ABR recordings to currently registered ABR dataset, and executing the operations of S1' to S5' repeatedly at the current loudness level;

wherein k is a preset fixed value, or a value obtained by calculating all data points according to a preset proportion.

Alternatively, in step A2, the operation of the adaptive average method comprises:

performing a parallel judgment on the ABR recordings that are time curves of which an input type is repeated single recording for Q times, executing steps S1 to S4 in each time;

S1, dividing currently registered ABR dataset into two groups randomly and calculating average curves respectively;

S2, calculating the cross-correlation function of the two group averages;

S3, obtaining the time lag where the maximum value of the cross-correlation coefficient is located;

S4, comparing an absolute value of the time lag with a value of k to judge whether a deviation of the time lag is within k data points:

if the absolute value of the time lag is less than the value of k, indicating that the deviation of the time lag is within the k data points, which denotes that a stable time-locked signal is detected; if the absolute value of the time lag is not less than the value of k, indicating that the deviation of the time lag is not within the k data points, which denotes that no stable time-locked signal is detected;

S5, judging whether the stable time-locked signal is detected each time in the parallel judgment for Q times:

if the stable time-locked signal is detected in each of the Q times, stopping the data acquisition, which corresponds to a case that the ABR signal is detected;

if the stable time-locked signal is not detected in each of the Q times, further executing step S6:

S6, judging whether a maximum number of iterations at the current loudness level is reached:

if the maximum number of iterations is reached, stopping the data acquisition, which corresponds to the case that no ABR signal is detected;

if the maximum number of iterations is not reached, further adding newly registered ABR recordings to current ABR dataset, and executing the operations of S1 to S6 repeatedly at the current loudness level;

wherein k is a preset fixed value, or a value obtained by calculating all data points according to a preset proportion.

Alternatively, in step A2, the operation of the adaptive average method comprises:

S1", the ABR dataset being a time curve of which an input type is multiple-averaged recordings; combining the average curve $avgA_{add}$ which is newly added in a present iteration with the average curve $avgA_{old}$ of previous iterations to update a weighted average curve $avgA_{new}$ $$avgA_{new} = \frac{(M-1) \times avgA_{old} + avgA_{add}}{M}$$

wherein Q groups of $avgA_{new}$, $avgA_{old}$, $avgA_{add}$ are provided, respectively; M is a current number of iterations;

S2", calculating the cross-correlation function between each two groups for the current average curve $avgA_{new}$ of the Q groups;

S3", obtaining time lags of the Q groups where the maximum value of the cross-correlation coefficient is located;

S4", in the parallel judgment for Q times, comparing an absolute value of the time lag of each group with a value of k to judge whether a deviation of the time lag is within k data points: if the absolute value of the time lag is less than the value of k, indicating that the deviation of the time lag is within the k data points, which denotes that a stable time-locked signal is detected; if the absolute value of the time lag is not less than the value of k, indicating that the deviation of the time lag is not within the k data points, which denotes that no stable time-locked signal is detected;

S5", judging whether the stable time-locked signal is detected each time in the parallel judgment for Q times:

if the stable time-locked signal is detected in each of the Q times, stopping the data acquisition, which corresponds to a case that the ABR signal is detected;

if the stable time-locked signal is not detected in each of the Q times, further executing step S6":

S6", judging whether a maximum number of iterations at the current loudness level is reached;

if the maximum number of iterations is reached, stopping the data acquisition, which corresponds to the case that no ABR signal is detected; if the maximum number of iterations is not reached, further adding newly registered ABR dataset to currently ABR test average data, and executing the operations of S1" to S6" repeatedly at the current loudness level;

wherein k is a preset fixed value, or a value obtained by calculating all data points according to a preset proportion.

Alternatively, the average times used in calculating the ABR recording average curve at each sound loudness level is a product of the number of iterations and a value of N; the value of N corresponds to the number of groups of the newly added ABR recordings at each iteration.

Alternatively, in step A6, after the number of iterations used at each sound loudness level is normalized, the sound loudness level corresponding to the hearing threshold is obtained by Sigmoid function fitting and interpolation.

Alternatively, the ABR recordings at each sound loudness level are animal experimental data or clinical data, obtained through real-time testing or stored offline; and the ABR recordings are preprocessed by one or more of: signal amplification; bandpass filtering; adjusting a time interval of ABR waveform acquisition, selecting an ABR time curve in a corresponding time interval after sound stimulation is started as an object of analysis; excluding an ABR time curve corresponding to background noise; removing low-frequency background noise by means of a smooth spline fitting function.

Another technical solution of the present invention is to provide an automatic test device for auditory brainstem response (ABR), which is used for any one of the above automatic routine for ABR test, the automatic test device for ABR test comprises:

an input module that acquires ABR recordings acquired at a stimulation of each sound loudness level;

a control module that drives the input module to acquire ABR dataset acquired in batches at the stimulation of each sound loudness level from an initial sound loudness level to a minimum loudness level;

an adaptive average method operation module that executes an operation of an adaptive average method to gradually increase the times of level averaging through iteration until conditions of ABR signal detection are met; the conditions of the ABR signal detection including: after grouping ABR dataset upon a current loudness level in a current iteration, respectively calculating an average response curve of each group according to current average times, obtaining a time lag where a maximum value of cross-correlation coefficient between the groups is located, and judging whether an ABR signal with time-locked characteristics exists based on the rule that whether a deviation of the time lag is within a specified data point range;

a storage module that stores the number of iterations used at each sound loudness level during the operation of the adaptive average method; and a main judgment module that judges whether the ABR signal is detected during the operation of the adaptive average method according to results output by the adaptive average method operation module; and when it is judged that the ABR signal is detected, further judges whether the current loudness level reaches a set minimum; or when it is judged that the ABR signal is not detected, further judges whether the ABR signal is not detected at successive P loudness levels;

wherein if it is judged that the minimum loudness level is not reached, the main judgment module issues an instruction to the control module, and the control module further drives the input module to acquire the ABR dataset at an updated loudness level; the updated loudness level is obtained by subtracting the step size from the current loudness level; or, if it is judged that the minimum loudness level is reached, the main judgment module issues an instruction to the control module, and the control module calls the number of iterations used in the adaptive average operation from the storage module; and the lowest loudness level required to detect the ABR signal is taken as the hearing threshold.

Alternatively, the automatic test device for ABR further comprises a function fitting module, which obtains the sound loudness level corresponding to the hearing threshold by the function fitting and interpolation on the number of executed iterations in the routines of the adaptive average method.

Alternatively, the adaptive average method operation module issues an instruction for collecting data to the control module, when a data type input by the input module is repeated single sweeps, the adaptive average method operation module executes one judgment or a plurality of parallel judgments corresponding to each iteration of each sound loudness level; in the one judgment or each judgment of the parallel judgments, currently registered ABR recordings are randomly divided into two groups to calculate an average curve of each group, after that a time lag corresponding to the maximum value of the cross-correlation coefficient is calculated, an absolute value of the obtained time lag is compared with a value of k to judge whether a deviation of the time lag is within k data points; if the absolute value of the time lag is less than the value of k, it denotes that a stable time-locked signal is detected; if the absolute value of the time lag is not less than the value of k, it denotes that no stable lock signal is detected;

if the stable time-locked signal is detected at the current loudness level in the one judgment or each judgment of the parallel judgments, the adaptive average method operation module issues an instruction to stop data acquisition to the control module, gives return information indicating that the ABR signal is detected at the current loudness level, and stores the current number of iterations through the storage module;

if no stable time-locked signal is detected at the current loudness level in the one judgment, or if the stable time-locked signal is not detected at the current loudness level in each judgment of the parallel judgments, the adaptive average method operation module further judges whether the maximum number of iterations at the current loudness level is reached:

if the maximum number of iterations is reached, the adaptive average method operation module issues the instruction to stop data acquisition to the control module, gives return information indicating that the ABR signal cannot be detected at the current loudness level, and stores the current number of iterations through the storage module; and if the maximum number of iterations is not reached, the adaptive average method operation module further issues an instruction to add new data to the control module, and after adding newly acquired data into original datasets, the operations of the adaptive average method are repeatedly executed at the current loudness level;

wherein k is a preset fixed value, or a value obtained by calculating all data points according to a preset proportion.

Alternatively, the adaptive average method operation module issues an instruction for collecting data to the control module, when a data type input by the input module is multiple average dataset, the adaptive average method operation module combines the average curve $avgA_{add}$ which is newly added in a present iteration with the average curve $avgA_{old}$ of previous iterations to update a weighted average curve $avgA_{new}$ $$avgA_{new} = \frac{(M-1) \times avgA_{old} + avgA_{add}}{M}$$

wherein $avgA_{new}$, $avgA_{old}$, $avgA_{add}$ are average data of ABR test of Q groups; M is a current number of iterations; the adaptive average method operation module calculates the cross-correlation function between each two groups for the weighted average curve $avgA_{new}$ of the Q groups, and obtained time lags of the Q groups where the maximum value of the cross-correlation coefficient is located;

in the parallel judgment for Q times, an absolute value of the time lag of each group is compared with a value of k to judge whether a deviation of the time lag is within k data points: if the absolute value of the time lag is less than the value of k, it indicates that the deviation of the time lag is within the k data points, which denotes that a stable time-locked signal is detected; if the absolute value of the time lag is not less than the value of k, it indicates that the deviation of the time lag is not within the k data points, which denotes that no stable time-locked signal is detected;

the adaptive average method operation module judges whether the stable time-locked signal is detected each time in the parallel judgment for Q times: if the stable time-locked signal is detected in each of the Q times, the adaptive average method operation module issues an instruction to stop data acquisition to the control module, gives return information indicating that the ABR signal is detected at the current loudness level, and stores the current number of iterations through the storage module;

if the stable time-locked signal is not detected in each of the Q times, the adaptive average method operation module further judges whether the maximum number of iterations is reached: if the maximum number of iterations is reached, the adaptive average method operation module issues the instruction to stop data acquisition to the control module, gives return information indicating that the ABR signal is detected at the current loudness level, and stores the current number of iterations through the storage module; and if the maximum number of iterations is not reached, the adaptive average method operation module further adds newly acquired ABR test average data to currently registered ABR test average data, and executes the operations of the adaptive average method repeatedly at the current loudness level;

wherein k is a preset fixed value, or a value obtained by calculating all data points according to a preset proportion.

In the traditional ABR test, the sound loudness level is tested from high to low, and each sound loudness level is repeated for a fixed number of times to obtain an averaged signal, the specialist judges that the lowest loudness level with auditory brainstem response is the hearing threshold (it is considered that when the sound loudness level is higher than the threshold, the brain reacts and it can be heard). For the past 30-40 years, in order to reduce misdiagnosis caused by artificial subjective judgment, the industry has been developing automatic hearing test methods, but no mature commercial products have come out, for the reason that the quantitative analysis of signals will be affected by experimental conditions (such as the degree of anesthesia, the placement of electrodes etc.). Therefore, it is difficult to have an absolute value (signal-to-noise ratio, correlation coefficient, etc.) that can be considered as having signal when above this value and no signal when below this value, and can correspond to the hearing threshold.

Compared with the prior art, the adaptive average algorithm provided by the present invention is used for analyzing data generated in the ABR-based hearing test, and can replace human to automatically acquire the hearing threshold (the main index of the hearing test) of the subject, wherein the repetition times of each sound loudness level can be dynamically adjusted. In other words, since there is no exact value that can correspond to the hearing threshold, a standard is set in advance, and then a problem of how many times it takes to reach this standard on average is solved.

In this regard, with the adaptive average algorithm of the present invention, for the ABR recordings acquired in batches from high to low test sound loudness levels, the times of level averaging are gradually increased through iteration to improve the signal-to-noise ratio until conditions of an ABR signal detection are met. According to the condition of the ABR signal detection, two groups of average curves are obtained by randomly grouping ABR recordings acquired in batches, the time lag corresponding to the maximum value of the cross-correlation coefficient is calculated, and whether an ABR signal with time-locked characteristics exists is judged based on the rule that whether the deviation of the time lag is within a specified range. The hearing threshold can be obtained as the minimum loudness level required to detect the signal, or the sound loudness level corresponding to the hearing threshold obtained by function fitting and interpolation on the number of executed iterations at each loudness level.

Using the cross-correlation function to judge, when there is a time-locked signal (ABR), the theoretical time lag is 0 (the actual calculation will deviate k data points, and k in the example is 1, corresponding to the full dot in FIG. 6); if there is no signal, the time lag is arbitrary (corresponding to the empty dot in FIG. 6). When using the adaptive average algorithm of the present invention, if the signal-to-noise ratio is high, the signal is detected without averaging for many times; if the signal-to-noise ratio is low, it needs to be averaged more times before the signal can be detected. The algorithm can dynamically adjust the average times. If there is no signal, the signal will not be detected even if it is averaged many times (we set an upper limit), as shown in FIG. 7.

On the other hand, the number of iterations required to detect the ABR signals at each sound loudness level acquired by the present invention can obtain more accurate hearing thresholds by function fitting and interpolation, improve an accuracy of threshold judgment, and effectively reduce the repeated acquisition times of ABR datasets. If the sound loudness level decreases by 5 dB, the accuracy of the traditional method is only 5 dB, but the present invention can reach 1 dB by function fitting (FIG. 8).

The present invention can also aim at two different input data types (FIG. 2 and FIG. 3), namely, data recorded in a signal repetition and averaged data, and these two data formats cover all clinical models for which the algorithm of the present invention can be applied.

With the method of the present invention, the accuracy rate with an error within ±5 dB is approximately 100%, and since a next sound loudness level is executed when the signal is detected at each sound loudness level, repetitive recording of up to 69% can be saved (FIGS. 10 and 11).

To sum up, the present invention provides an operation model of the adaptive average method, thereby realizing an efficient and reliable automatic routine for ABR test, the accuracy rate of the hearing threshold obtained by the method is close to the manual judgment of professionals, and is more objective and has better repeatability. More importantly, the method of the present invention does not need to adjust the model according to the data quality during use, so it has a wide application prospect in various clinical and scientific research ABR tests. At the same time, it is also worth mentioning that the method of the present invention can terminate the iteration according to the judgment result and feed it back to the hardware in real time, which not only can shorten the testing time and avoid the waste of storage space, but also can be used as a core module for an unmanned fully automated ABR hearing test device, which is expected to completely free clinicians from the hearing test task.

DETAILED DESCRIPTION OF THE EMBODIMENTS

Figure 1:
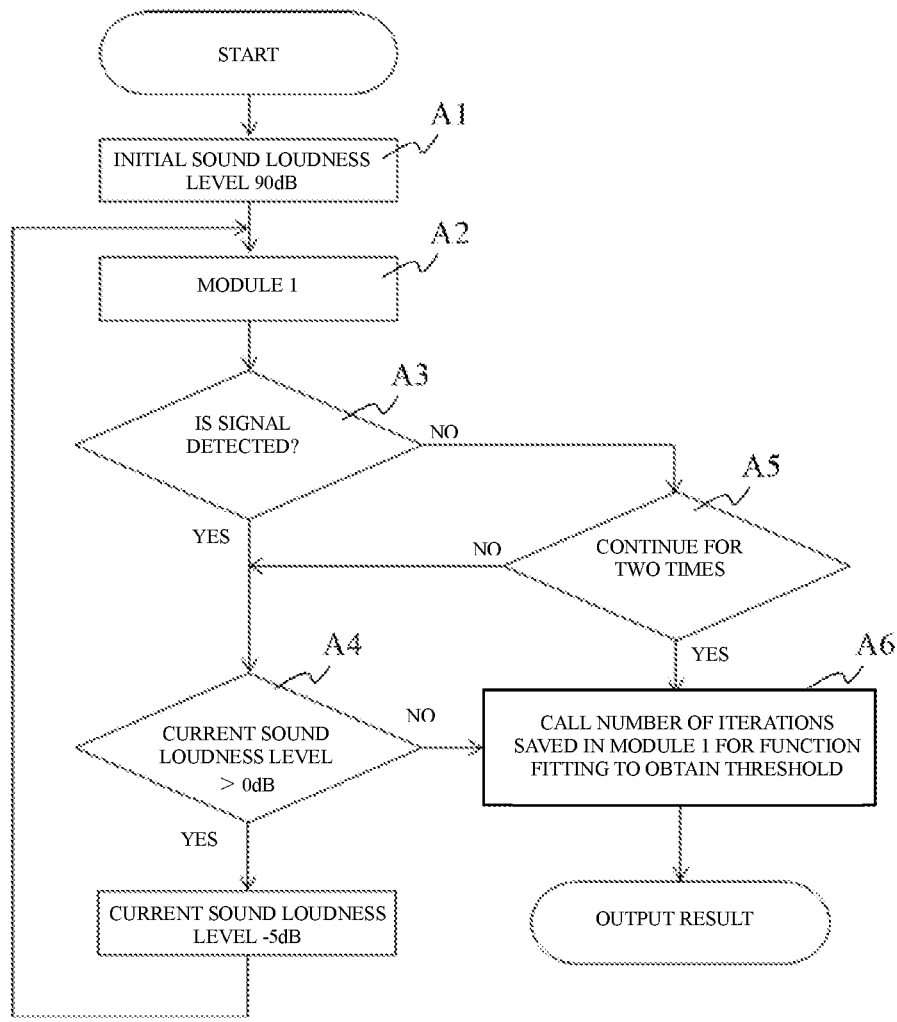
FIG. 1 is a flowchart of an automatic test method for auditory brainstem response of the present invention.

For a given sound stimulus (click and tone burst are commonly used), the auditory system will produce a series of potential responses. Auditory brainstem response (ABR) is used to record waveform changes of these potentials and extracts them from various strong noise backgrounds using various digital signal processing algorithms, so as to obtain auditory brainstem evoked potentials, which are important indicators for evaluating the integrity of auditory conduction system and monitoring the function of nervous system.

The present invention provides an algorithm model based on an adaptive average method, which can automatically process data signals obtained in ABR test, thereby realizing an automatic test device and method for auditory brainstem response.

Firstly, the traditional test mode and the principle involved in the present invention are briefly described:

in the traditional way, the original recordings obtained by the ABR test are analyzed by specialists: each test sound loudness level is repeated for a fixed number of times to test, and multiple smoothed time curves are obtained. Originally, based on the above data, specialists judged which sound loudness level was the minimum but still had auditory brainstem response, and used it as the hearing threshold, and considered that when the sound loudness level is higher than the threshold, it can be heard.

After analyzing the data, it is found that when the stimulus sound loudness level is less than the hearing threshold, the correlation coefficient between ABR recordings is symmetrically distributed around 0 (irrelevant); However, when the stimulus sound loudness level is higher than the hearing threshold, the distribution of correlation coefficient shifts to +1 direction (positive correlation). Empirical judgment of the minimum correlation coefficient required to detect a stable ABR waveform can be used as a criterion for judging the threshold (described in detail below).

However, in practice, the difference in data signal-to-noise ratio caused by different experimental conditions (e.g., the placement of electrodes, the degree of anesthesia of animals, etc.) affects the modeling of correlation coefficients, so each recording needs to be calibrated to guarantee the accuracy of its threshold judgment, which affects the practical value. To address the above problems, the present invention proposes to use the classical judgment criterion of time-locked signals (i.e., the time lag at the maximum of the cross-correlation coefficient is 0) to adjust the signal-to-noise ratio by changing the average times to finally achieve the dynamic detection of ABR signals, which is called the adaptive average method. That is, the present invention dynamically adjusts the repetition times of each sound loudness level, establishes a standard corresponding to the hearing threshold, and judges how many average times are needed to reach the standard by the adaptive average method, thus obtaining the hearing threshold.

Therefore, in the specific algorithm of the adaptive average method, the present invention uses the cross-correlation function to judge whether there is a time-locked signal (ABR), and the theoretical time lag is 0 when there is a signal (the actual calculation will deviate k data points, and k in the example is 1), or when there is no signal, the time lag is arbitrary.

Figure 2:
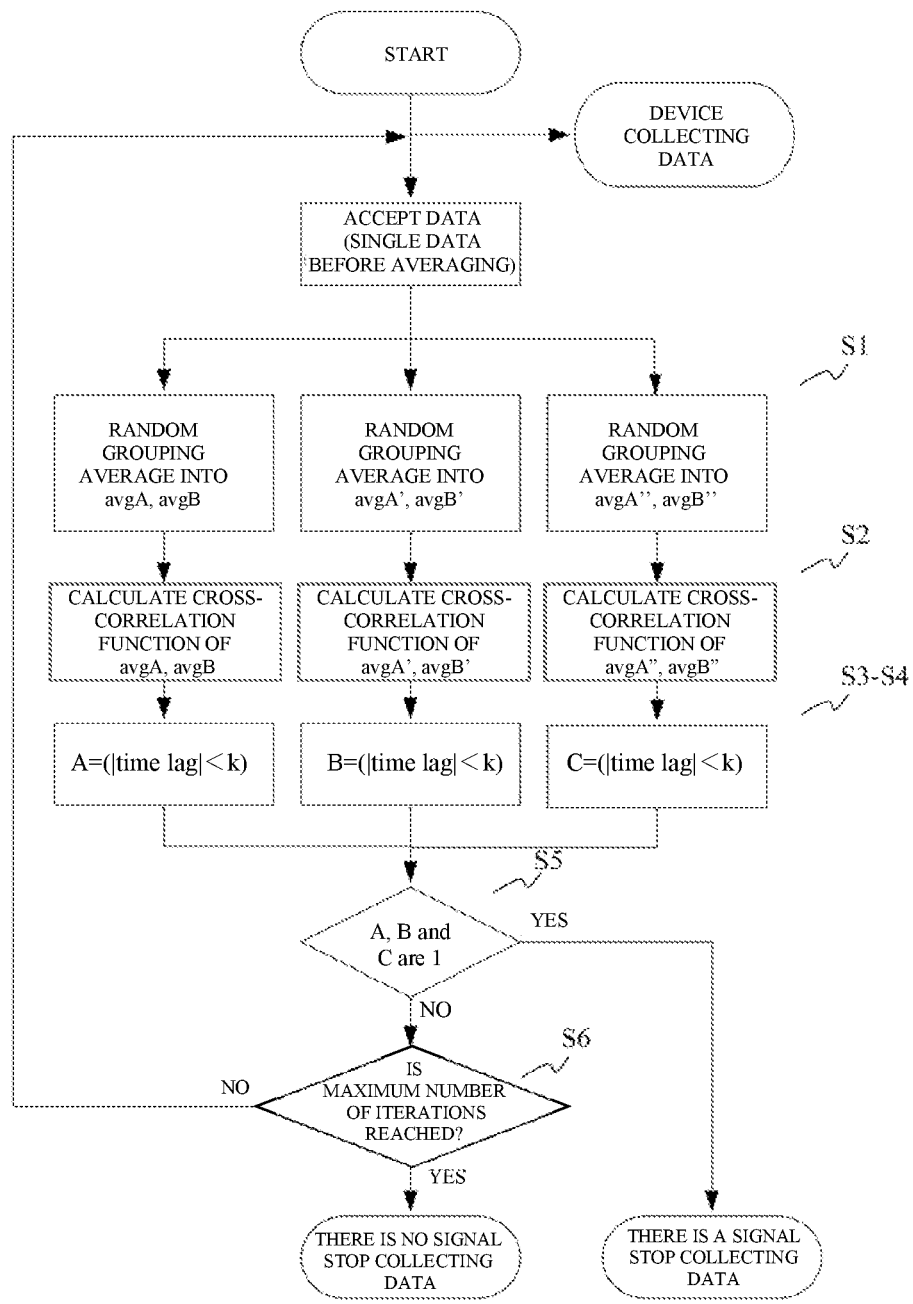
FIG. 2 is a flowchart of Module 1 when an input data type is single recording.
Figure 3:
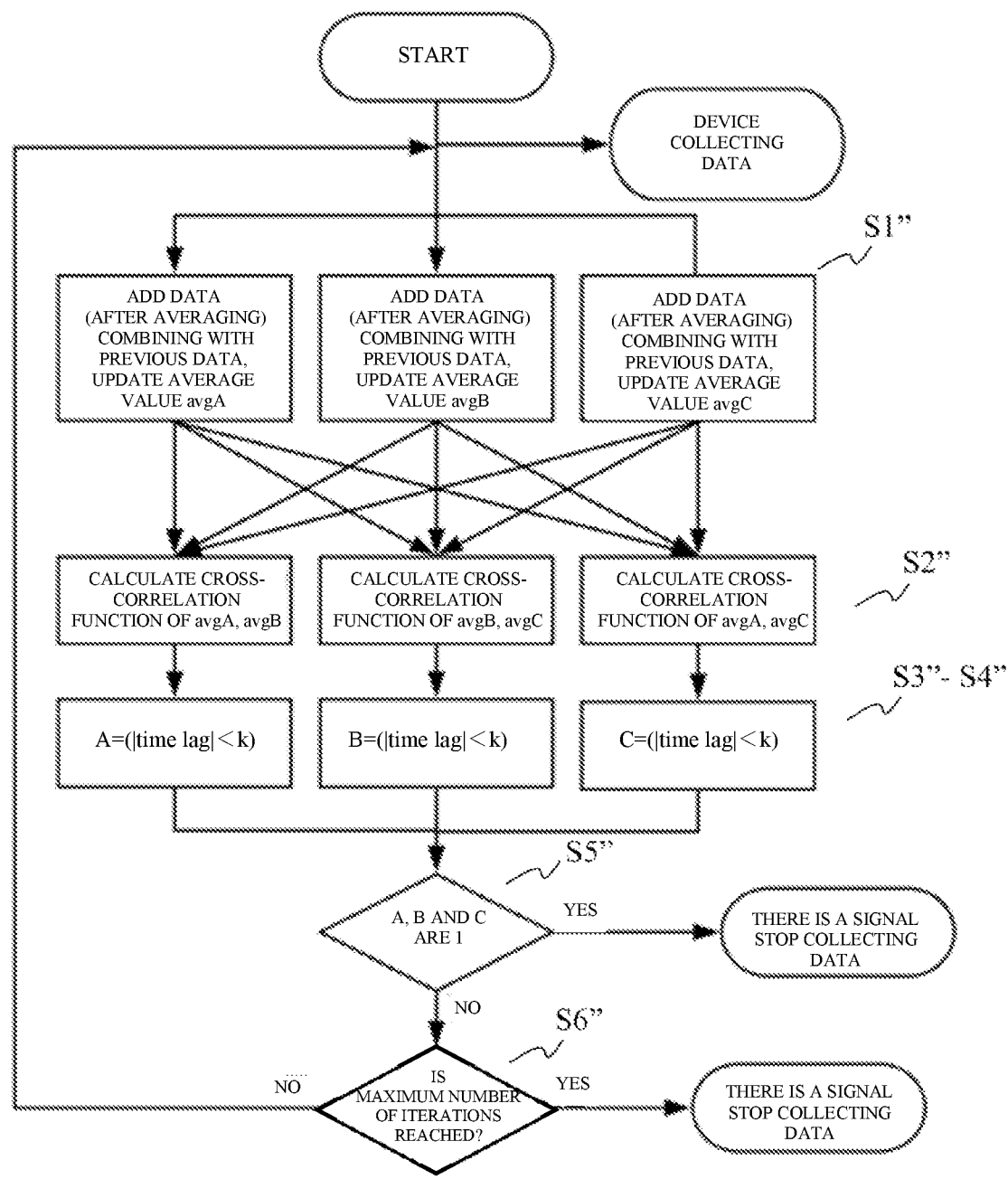
FIG. 3 is a flowchart of Module 1 when the input data type is averaged data.

In an example of FIG. 2, the present invention takes a random grouping average operation on data recorded by a single sound stimulus (while another example of FIG. 3 is applicable where only average data can be derived, as detailed below), using "whether the time lag of the maximum value of cross-correlation coefficient deviates within a data recording point" (generally, 1 data point is less than 50 microseconds due to systematic error) to judge whether there is a time-locked ABR signal; if no signal is detected, the data amount is gradually increased through iteration until the signal appears or reaches a preset maximum value.

The actual test results of the above detection method show that when the stimulus sound loudness level is higher than the hearing threshold, the average times required to meet the time lag condition remains at a relatively low level; however, when the stimulus sound loudness level approaches the threshold, the average times required increases exponentially; when the stimulus sound loudness level is lower than the threshold, a preset maximum number is reached, and the hearing threshold is the highest sound loudness level at which no signal is detected. It can be seen that when the adaptive average method of the present invention is used, if the signal-to-noise ratio is high, the signal is detected without averaging for many times; if the signal-to-noise ratio is low, the signal can be detected after averaging for more times; and since an upper limit is set, if there is no signal, the signal will not be detected even if it is averaged many times.

As shown in FIG. 1, the automatic test method for auditory brainstem response of the present invention includes:

A1, providing sound stimulation from an initial sound loudness level, and collecting corresponding ABR data through a device;

in present example, the ABR data of mice were used, during the experiment, the sound loudness level of stimulation ranged from high to low (90 dB to 0 dB) with an interval of 5 dB.

A2, judging whether it is necessary to continue collecting data to increase average times or interrupting the collection through an operation of an adaptive average method (corresponding to Module 1).

Figure 6:
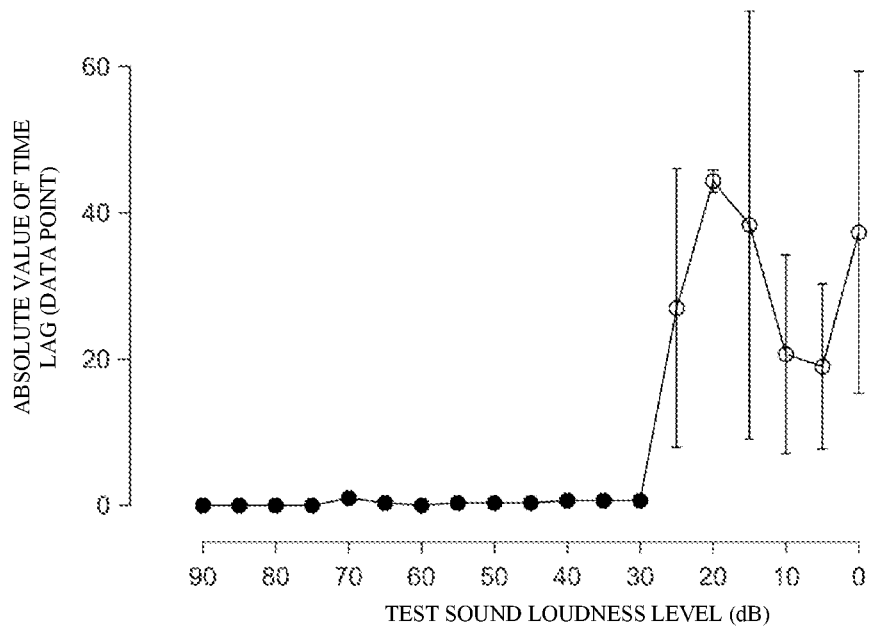
FIG. 6 shows a time lag corresponding to a maximum correlation coefficient obtained in iterations.

The operation of the adaptive average method (described in detail below) is to divide the current ABR data into any two groups using random grouping average and calculate the average curves respectively, obtain the time lag corresponding to the maximum value of the cross-correlation coefficient of the two groups of average curves, and judge whether a stable time-locked signal exists by judging whether the absolute value of the time lag is less than k data points by gradually increasing the recordings times to the maximum number of iterations (the iteration is terminated when the signal is detected or the maximum number of iterations is reached but there is still no signal). K is a fixed value corresponding to a fixed number of data recording points, or k is a value calculated according to a certain ratio (for example, 1% of all data points); and k=1 is used as an example for illustration and experimental verification below). Experimental data can confirm that the absolute value of time lag is maintained at a level less than k=1 when it is greater than the hearing threshold (FIG. 6).

A3, judging whether the ABR signal is detected in step A2: if the signal is detected, step A4 is executed; if the signal is not detected, step A5 is executed;

A4, judging whether the current loudness level reaches a set minimum loudness level (0 dB in present example); if the minimum loudness level is not reached, an updated loudness level is obtained by subtracting the interval (5 dB) from the current loudness level, and the corresponding sound stimulus is given, and the operation of A2 is re-executed; if the minimum loudness level is reached, step A6 is executed;

A5, judging whether the ABR signal is not detected for successive P sound loudness levels (the value of P in present example is set to be 2, which can be adjusted according to actual situations): if the signal is not detected for the successive P sound loudness levels, step A6 is executed; otherwise, turning to step A4; and A6, calling the number of iterations used in the adaptive average method, to obtain a threshold by function fitting.

In present example, the number of iterations at each sound loudness level is used as output (FIG. 7), and fitted by Sigmoid function after normalization (FIG. 8), $$f(x) = \frac{1}{1 + e^{-a(x-T)}}$$

that is, coefficients a and T can be obtained, according to the data verification at 1 dB interval (see the inset in FIG. 8), when $f(x)=0.9$, x is the threshold, the result is consistent with the threshold judged manually.

In Step A1, acquisition and preprocessing of the ABR data include:

(1) animal experiment: ABR data of mice stimulated by tone bursts (frequency 16 kHz, duration 3 milliseconds) from 90 to 0 dB (5 dB interval) were acquired by TDTRZ6/BioSigRZ system (the original signal was amplified by 20000 times and filtered through a band-pass filter of 50-5000 Hz). Each sound loudness level was recorded 500 times, the stimulation signal rate was 21 times/second, the data acquisition frequency was 21 kHz, and the acquisition time interval was 0-15 milliseconds after the sound stimulation.

In the TDTRZ6/BioSigRZ system, a TDT auditory evoked potential workstation is composed of an RZ6 processor, a preamplifier and BioSigRZ experiment design and analysis software. The workstation can record various bioelectrical signals including brainstem evoked potentials and otoacoustic emissions with low impedance electrodes, needle electrodes and surface electrodes.

Clinical: Data is derived from the NIH-funded Shared Record (www.physionet.org). ABR records stimulus tones (1 kHz or 4 kHz tone burst, stimulation rate 24 time/second) from 100 dB to 30 dB (5 dB interval) through monaural, and the electrodes of the subjects were arranged as follows: the recording electrode was placed on the forehead, the reference electrode was placed on the mastoid bone behind ear at the same side of the stimulating ear, and a ground electrode was placed on the mastoid bone at an opposite side of the stimulating ear. Each sound loudness level was recorded for 1000 times, the ABR signal was band-pass filtered from 30 Hz to 3000 Hz and amplified by an amplifier for 50000 times before recording, the sampling rate of the recording device was 48 kHz, and the acquisition time interval was 0-15 milliseconds after the sound stimulation The acquisition of ABR data from the above animal experiment and clinical and the recorded parameters during the pretreatment are only examples, and can be adjusted according to the specific application.

(2) According to the time interval corresponding to the ABR waveform, the ABR time curve between 0-6 milliseconds (mouse) or 5 to 15 milliseconds (clinical) after the start of sound stimulation was selected as the object of analysis. The time interval here is an empirical value, which can be adjusted according to the actual situation.

(3) The background noise caused by muscle activity or breathing can be eliminated by removing the time curve greater than 11 microvolts or less than −11 microvolts (the step is optional, and the parameter values involved depend on the settings of the hardware used).

(4) The low-frequency background noise is removed through the smoothing spline fitting function (the step is optional, and the smoothing parameter of the example is 0.5).

For example, after the obtained ABR data of the mouse are processed as described above, 350 curves are taken at each sound loudness level, and the correlation coefficient distribution between any two groups of curves can be calculated. The calculation formula is as follows:

$$R(A, B) = \frac{1}{N-1} \sum_{i=1}^{N} \left(\frac{Ai - \mu A}{\sigma A}\right)\left(\frac{Bi - \mu B}{\sigma B}\right)$$

$$A, B \in M, 且 A \neq B$$

where A and B are data of single recording; N is the number of data points recorded; μA and μB are average curves of single recording; σA and σB are standard deviations of single recording, and M is the number of iterations.

A median of the correlation coefficient of each loudness level is plotted, it can be seen that the correlation coefficient of the sound loudness level above the hearing threshold is larger than that below the hearing threshold.

In the traditional way, according to the threshold judged by the clinician, the median of the correlation coefficient corresponding to the vicinity of the threshold is plotted, and the correlation coefficient corresponding to the hearing threshold (approximately 0.01 in the example) can be obtained by aligning the curves of the corresponding normal mice and the corresponding deafness high-risk mice. However, the signal-to-noise ratio obtained from different experiments is different (background noise reduces the measured correlation coefficient), which leads to poor coincidence between the obtained curves and limits the accuracy of judging threshold. In the present invention, the minimum average times required for detecting the ABR signals at different signal-to-noise ratios are different, and the average times are dynamically adjusted according to the signal-to-noise ratios of different test sound loudness levels through the operation of the adaptive average method, so that the automatic test for the auditory brainstem response is realized, and the problems existing in manual judgment can be effectively solved.

Figure 5:
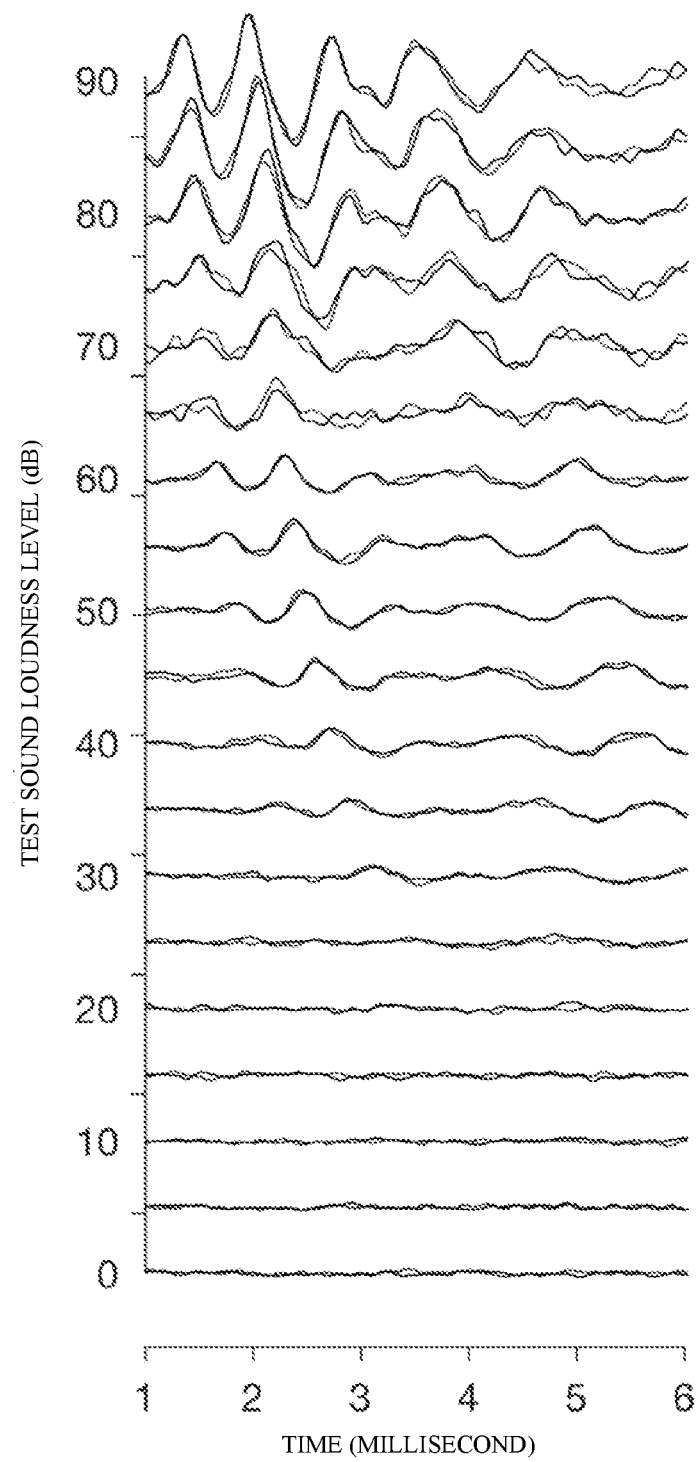
FIG. 5 shows results obtained by applying the adaptive average method to a same set of data, wherein two curves corresponding to each sound loudness level are average curves for calculating cross-correlation function.

Two embodiments of the operation of the adaptive average method (corresponding to Module 1) in step A2 of the present invention are described below:

as shown in FIG. 2, in an embodiment in which the input data type is repeated single recording, the operation of the adaptive average method of the present invention includes the following process:

S1, dividing the currently acquired ABR data into two groups at random, and calculating an average curve for each group to obtain an ABR time curve corresponding to the average curve of each group of data (such as two curves at each sound loudness level in FIG. 5);

S2, calculating the cross-correlation function of the two groups after being averaged respectively;

S3, obtaining the time lag corresponding to the maximum value of the cross-correlation coefficient;

S4. comparing an absolute value of the time lag with k=1:
if the absolute value of the time lag is less than 1, which indicates that a stable time-locked signal is detected (corresponding to each full dot in FIG. 6); and if the absolute value is not less than 1, which indicates that the stable time-locked signal is not detected (corresponding to each empty dot in FIG. 6).

In the present invention, parallel judgmental can be performed for many times, and steps S1 to S4 are executed each time, so as to avoid the problem that the background noise has a time lag which meets the requirement under a very occasional condition. In the example, the parallel judgment was made three times, and the three times were randomly averaged into avgA, avgB; avgA', avgB'; avgA", avgB" at random, the cross-correlation coefficients between avgA and avgB, between avgA' and avgB', and between avgA" and avgB" respectively to obtain the corresponding time lags, and the judgment result when the absolute value of the time lag is less than 1 (data point) is recorded as "1" and the judgment result when the absolute value of the time lag is not less than 1 (data point) is recorded as "0"; The operation of the adaptive average method of the present invention further includes the following process:

S5, if the three times of judgment all indicate that the stable time-locked signal is detected at the current loudness level, that is, the judgment results corresponding to the three times of judgment A, B and C are all "1", the data collection can be stopped, which indicates that the stable time-locked signal can be detected at the current loudness level, and the test is passed at the present loudness level;

otherwise, if the judgment results corresponding to the three judgments A, B and C are not all "1", the following process is executed:

S6, judging whether a maximum number of iterations at the sound loudness level is reached:

that is, judging whether $M=M_{max}$ is satisfied, wherein $M_{max}$ is the preset maximum number of iterations; M is the current number of iterations, and M is incremented by 1 each time step S1 is executed; if $M<M_{max}$, the iteration continues;

if the maximum number of iterations is reached, the data collection can be stopped, which means that the stable time-locked signal cannot be detected at the current loudness level, and the test is not passed at the current loudness level; if the maximum number of iterations is not reached, N groups of newly acquired data (N=50 in the example) are further added to the original data, and the process of steps S1-S6 is repeated at the present loudness level.

Figure 4:
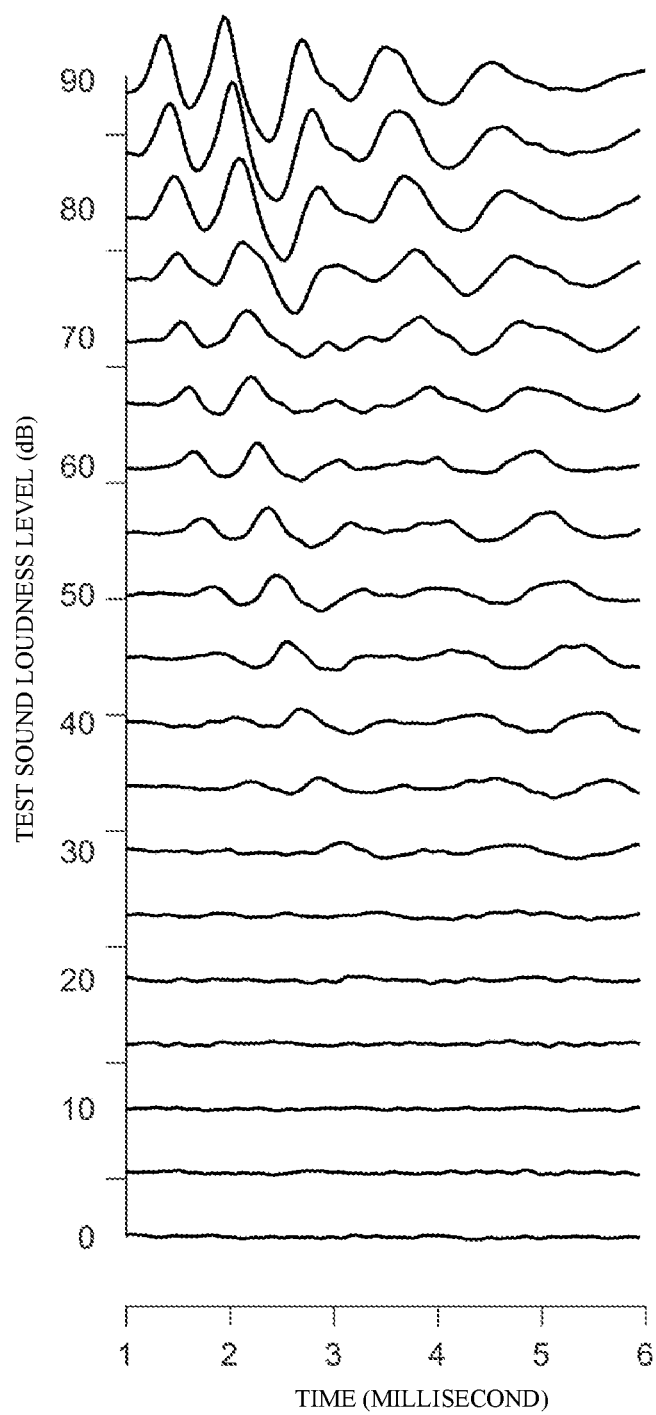
FIG. 4 shows ABR time curves of mice after averaging for 350 times at each sound loudness level.
Figure 7:
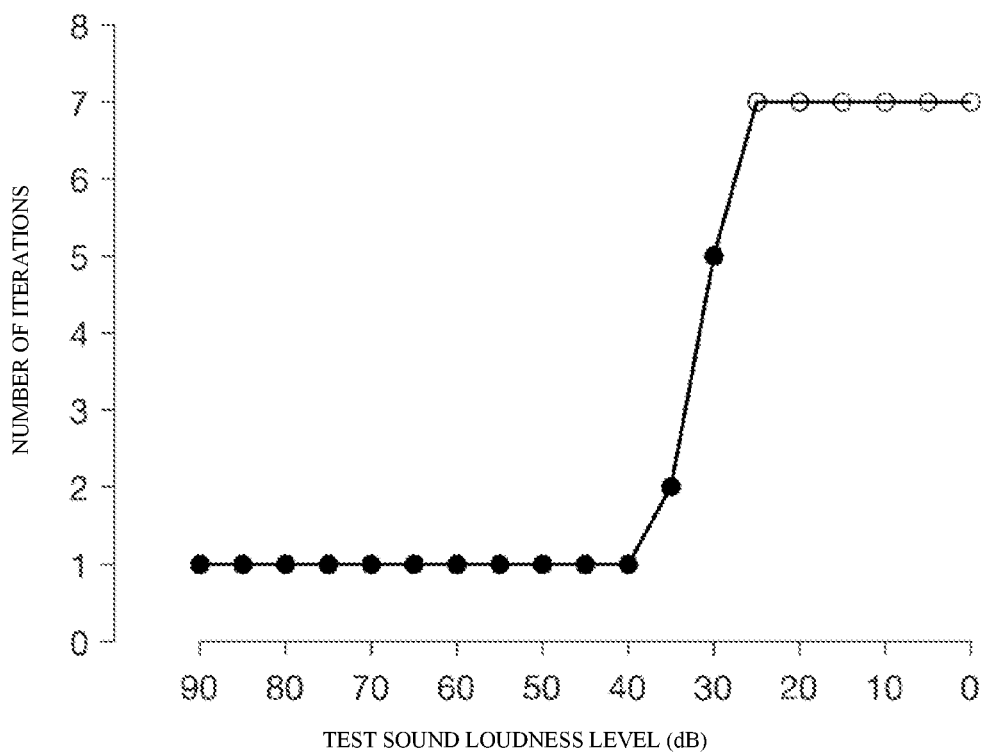
FIG. 7 shows number of iterations required to detect signals at each sound loudness level.

FIG. 4 shows ABR time curves of mice after averaging for 350 times at each sound loudness level; FIG. 5 is a result obtained by using the same set of data of FIG. 4 through the adaptive average method, the black lines/gray lines at each sound loudness level are two sets of average curves used to calculate the cross-correlation function, and the average times used for each sound loudness level is a product of the current number of iteration M and N shown in FIG. 7 (in the example is ×50); FIG. 6 shows the time lag (absolute value) corresponding to the maximum correlation coefficient obtained in the iteration, the full dot denotes that the stable time-locked signal is detected, and the empty dot denotes that the stable time-locked signal is not detected. According to the interval of the corresponding sound loudness levels when the full dot jumps to the empty dot in FIG. 6, it is known that the hearing threshold of the example is between 25 to 30 dB. FIG. 7 shows the number of iterations required to detect the signal at each sound loudness level. If no signal is set for two consecutive times (reaching the maximum number of iterations), it means that it has been lower than the hearing threshold, and the test is automatically terminated, the full dot in the figure is the actual test sound loudness level and the empty dot is the sound loudness level without test (since the test can be terminated in principle after no signal is detected for two times).

Figure 10:
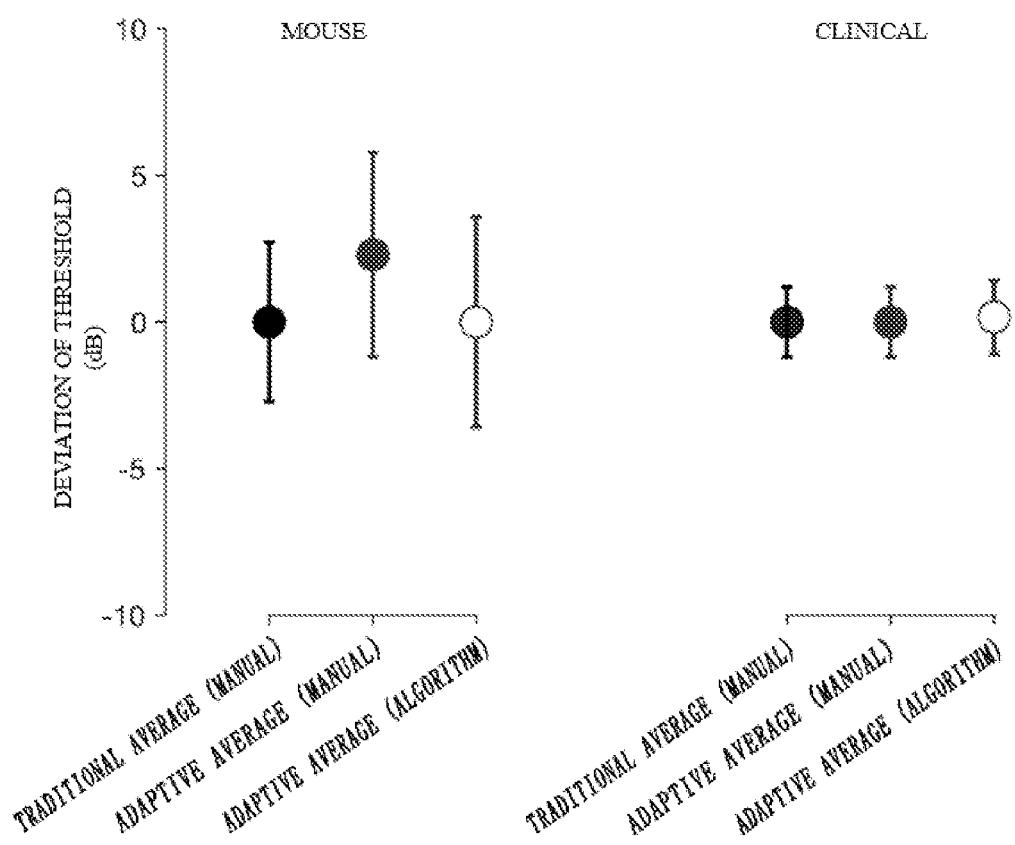
FIG. 10 shows a comparison of deviations of thresholds obtained by specialist reading test data using a traditional average method, the specialist reading data required by an adaptive algorithm and a machine applying the adaptive algorithm of the present invention.
Figure 11:
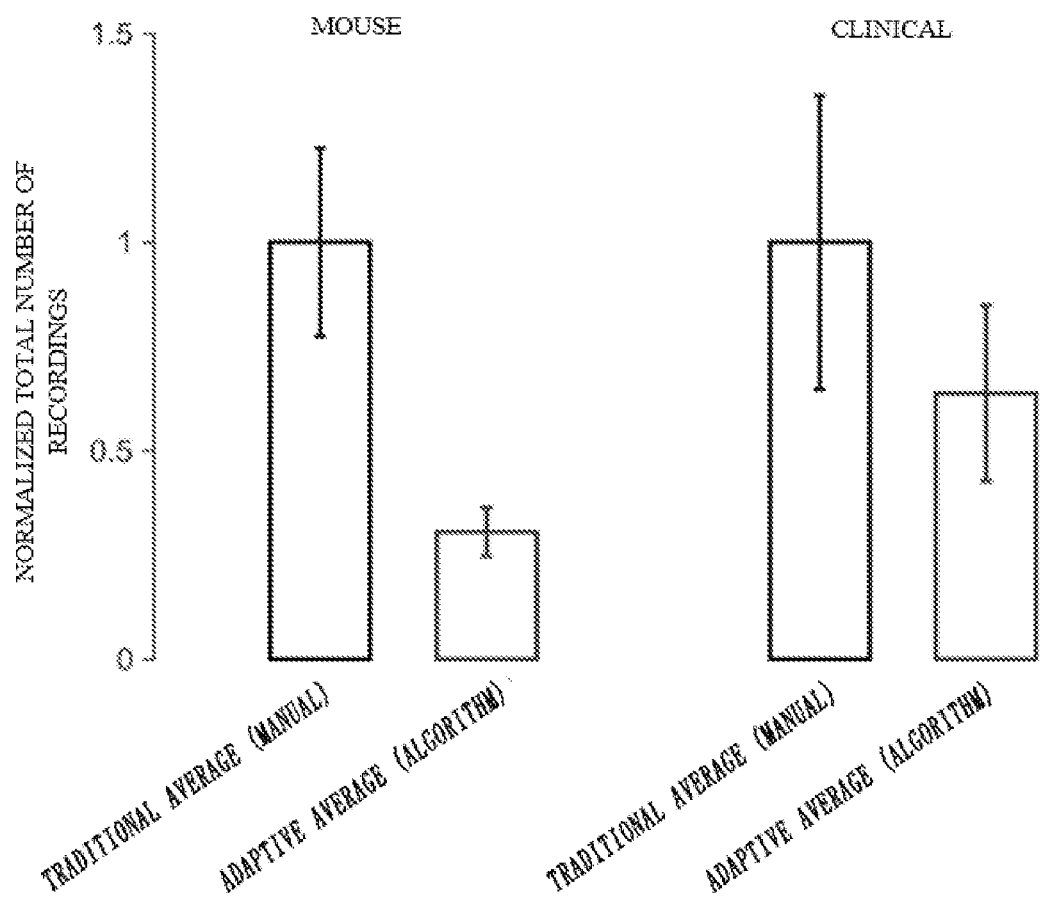
FIG. 11 is a comparison of normalized total number of recordings obtained by the specialist reading test data using a traditional average method and the machine applying the adaptive algorithm of the present invention.

As shown in FIG. 10 (the left group and the right group correspond to animal experimental data and clinical experimental data, respectively), deviations of the threshold obtained by performing threshold judgment to the average curves of all the data read by specialists in a traditional way, to the data obtained by the specialist reading the average times of the adaptive algorithm of the present invention, and the data obtained by a machine using the average times of the adaptive algorithm of the present invention are compared. As shown in FIG. 11 (the left group and the right group correspond to animal experimental data and clinical experimental data respectively), the normalized number of data pieces (i.e., the total number of recordings) of all data required by specialists for threshold judgment in the traditional way is compared with the normalized number of data pieces required for threshold judgment by the adaptive algorithm of the present invention.

As shown in FIG. 10 and FIG. 11, compared with the average curve of hearing threshold determined by a plurality of specialists, the accuracy rate of the method of the present invention is basically 100% with an error within ±5 dB. In addition, compared with using a preset maximum average time for each sound loudness level, the present invention can reduce the recordings that do not contribute to the threshold judgment by up to 69% because the next sound loudness level test is performed as soon as a signal is detected for each sound loudness level.

Figure 8:
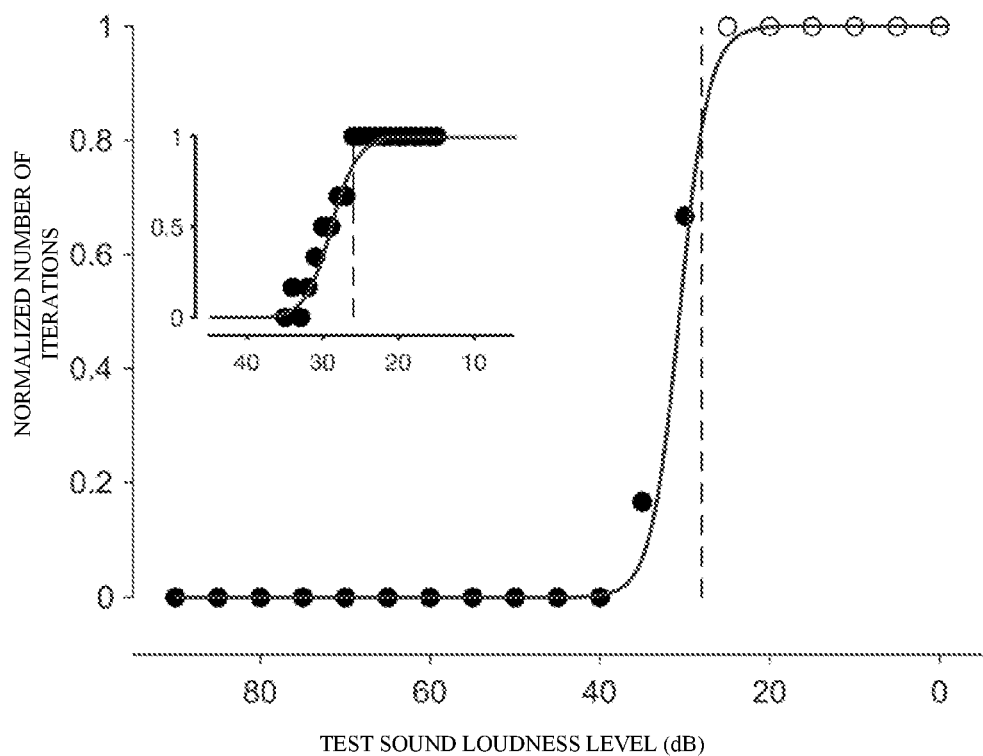
FIG. 8 shows corresponding thresholds obtained by fitting normalized number of iterations by Sigmoid function.

The present invention can further improve the accuracy of the hearing threshold judgment through function fitting. FIG. 8 shows the normalized number of iterations, through Sigmoid function fitting and interpolation (corresponding to step A6), to obtain the sound loudness level corresponding to the hearing threshold, and (insert) ABR detection results with 10 dB up and down near the threshold and 1 dB interval, the threshold obtained in the example is 26 dB. That is to say, if the test sound loudness level is decreased by 5 dB, the traditional method only has an accuracy of 5 dB, but the present invention can achieve 1 dB through function fitting.

For the case that only average data can be derived, in another embodiment as shown in FIG. 3, the operation of the adaptive average method of the present invention (the input data type is multiple average recordings) is different from the previous embodiment in that:

three groups of average data acquired continuously are added in each iteration (for example, the average times of each group is 50 times; the number of groups corresponds to the times of parallel judgment), and the average curve is recalculated according to the weight in combination with the previous data; for example, for the fourth iteration:

$$avgA(\text{new}) = \frac{3 \times avgA(\text{old}) + avgA(\text{add})}{4}$$

avgA (new) is the updated average curve;
avgA (old) is the average curve of the previous iteration;
avgA (add) is the newly added average curve;
for the current three groups of updated average curves, the cross-correlation function between each two groups is calculated, and three groups of time lag corresponding to the maximum value of the cross-correlation coefficient are obtained, and the judgment of the absolute value of the time lag with k=1 (data point) is executed. If the three groups of judgment all indicate that the stable time-locked signal is detected at the current loudness level, the data collection can be stopped, which indicates that the stable time-locked signal can be detected at the current loudness level, and the test is passed at the present loudness level; otherwise, it is further judged whether the maximum number of iterations at the sound loudness level is reached: if the maximum number of iterations is reached, the data collection is stopped, which means that the stable time-locked signal cannot be detected at the current loudness level, and the test is not passed at the current loudness level; if the maximum number of iterations is not reached, new average data is added to the original average data to repeat the above process.

Figure 9:
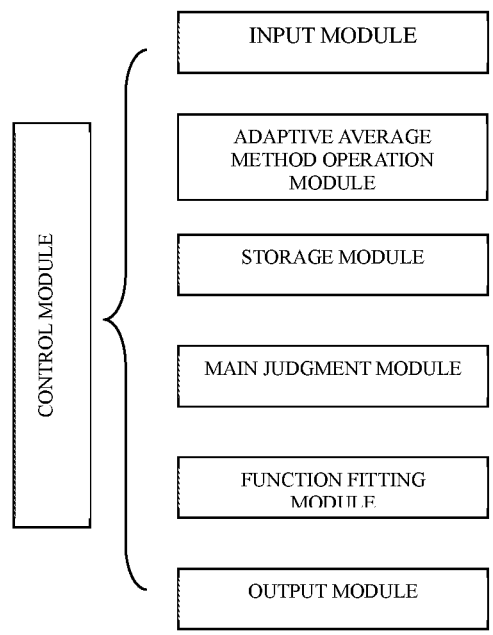
FIG. 9 is a schematic block diagram of an automatic test device for auditory brainstem response of the present invention.

As shown in FIG. 9, the present invention further provides an automatic test device for auditory brainstem response, which comprises:

an input module that acquires ABR data at a stimulation of each sound loudness level, to input into the device; wherein a type of input data can be repeated single recording or multiple average recordings; the data input module can be connected with an auditory brainstem evoked potential acquisition equipment to obtain real-time ABR data detected from the subject, and can also obtain experimental data from some storage equipment for offline processing;

a control module that drives the input module to acquire the ABR data at the stimulation of corresponding sound loudness level; wherein for example, according to different stages of the test, recording ABR time curves from the initial sound loudness level to the minimum loudness level (in the example, it is from 90 dB to 0 dB, and an interval is 5 dB); when acquiring the real-time data, the control module can drive a sound stimulation generator to gradually adjust the sound loudness level and provide corresponding sound stimulation signals to the subject; when acquiring the offline data, the control module can drive the input module to acquire more sets of experimental data according to the test process;

an adaptive average method operation module (corresponding to Module 1) that judges whether it is necessary to continue acquiring newly data to increase average times or interrupting the acquisition, wherein depending on the type of input data, the adaptive average method operation module may execute the operation flow as shown in FIG. 2 based on repeated single recording or the operation flow as shown in FIG. 3 based on multiple average recordings;

a storage module that stores the number of iterations used at each sound loudness level during the operation of the adaptive average method; and a main judgment module that judges whether the ABR signal is detected during the operation of the adaptive average method according to results output by the adaptive average method operation module, when it is judged that a signal is detected, further judges whether the current loudness level reaches a set minimum loudness level; or when it is judged that the signal is not detected, further judges whether the ABR signal is not detected at successive P loudness levels;

wherein if it is judged that the minimum loudness level is not reached, the main judgment module issues an instruction to the control module, and the control module further drives the input module to acquire corresponding ABR data at an updated loudness level (the updated loudness level is obtained after the current loudness level subtracts the interval (5 dB)); or, if it is judged that the minimum loudness level is reached, the main judgment module issues an instruction to the control module, and the control module calls the number of iterations used in the adaptive average operation from the storage module, and sends it to a function fitting module to obtain the threshold through function fitting.

In the function fitting module of the example, according to the number of iterations at each sound loudness level in the operation process of the adaptive average method (FIG. 7), after normalization, the Sigmoid function is used for fitting (FIG. 8), and the sound loudness level corresponding to the hearing threshold is obtained by interpolation.

An output module can acquire the corresponding process parameters, calculation results, judgment conclusions and other information from other modules, and output the data or charts of each stage of the test as required (as shown in FIG. 4 to FIG. 8), which is convenient for technicians to observe or store recordings. For example, the ABR time curve can be provided for each set of data averaged from the ABR data acquired at a stimulation of each sound loudness level obtained by the input module; According to the operation conclusions of the adaptive average method, two sets of average curves used to calculate the cross-correlation function at each sound loudness level, the time lag corresponding to the maximum correlation coefficient obtained by iteration when the stable time-locked signal is detected or not detected, the sound loudness level interval corresponding to the hearing threshold, the number of iterations required for detecting the signal at each sound loudness level, and the threshold obtained by function fitting and interpolation for the number of iterations of normalization, etc.

The adaptive average method operation module executes the operation flow shown in FIG. 2 based on the repeated single recording, issues a data collection instruction to the control module (thereby the control module drives the input module to acquire the corresponding sound loudness level and the corresponding type of test data); the adaptive average method operation module randomly divides the currently acquired ABR data into two groups to calculate the average curve of each group and then calculates the time lag corresponding to the maximum value of the cross-correlation coefficient, and compares the absolute value of the time lag with k=1 (data point): if the absolute value of the time lag is less than 1, it means that a stable time-locked signal is detected; and if the absolute value of the time lag is not less than 1, it means that no stable time-locked signal is detected.

Preferably, the adaptive average method operation module can perform parallel judgment for many times, when each time of the parallel judgment indicates that the stable time-locked signal is detected at the current loudness level, an instruction to stop collecting data is issued to the control module (thereby the control module drives the input module to stop acquiring data), and a signal indicating that the stable time-locked signal cannot be detected at the current loudness level and the test is not passed at the current loudness level is returned;

otherwise, if not each time of the parallel judgment indicates that the stable time-locked signal is detected at the current loudness level, then it is further judged whether the maximum number of iterations under the sound loudness level is reached: if the maximum number of iterations is reached, an instruction to stop collecting data can be issued to the control module, and a signal indicating that the stable time-locked signal cannot be detected at the current loudness level and the test is not passed at the current loudness level is returned; if the maximum number of iterations is not reached, an instruction to add new data is further issued to the control module (thereby the control module drives the input module to continue to acquire data, and 50 groups of newly acquired data are added in the example); after the newly acquired data is added to the original data, the adaptive average method operation module repeatedly executes the above operation process at the current loudness level.

Alternatively, the adaptive average method operation module executes the operation flow shown in FIG. 3 based on the multiple average recording, issues a data collection instruction to the control module (thereby the control module drives the input module to acquire the corresponding sound loudness level and the corresponding type of test data); the adaptive average method operation module combines the three groups of average data acquired continuously that are added in each iteration (for example, the average times of each group is 50 times; the number of groups corresponds to the times of parallel judgment) with the previous data to recalculate the average curve according to the weight; for the current updated average curves of the groups, the cross-correlation function between each two groups is calculated, and multiple groups of time lag corresponding to the maximum value of the cross-correlation coefficient are obtained, and the judgment of the absolute value of the time lag with k=1 (data point) is executed.

If the groups of judgment all indicate that the stable time-locked signal is detected at the current loudness level, an instruction to stop collecting data can be issued to the control module (the control module drives the input module to stop collecting data), and a signal indicating that the stable time-locked signal can be detected at the current loudness level and the test is passed at the current loudness level is returned; otherwise, it is further judged whether the maximum number of iterations at the sound loudness level is reached: if the maximum number of iterations is reached, an instruction to stop collecting data can be issued to the control module, and a signal indicating that the stable time-locked signal cannot be detected at the current loudness level and the test is not passed at the current loudness level is returned; if the maximum number of iterations is not reached, an instruction to add new data is further issued to the control module; after the new average data is added to the original average data, the adaptive average method operation module repeats the above operation process at the current loudness level.

It can be understood that the input module, control module, adaptive average operation module, storage module, main judgment module, function fitting module, output module, etc. of the automatic testing device for auditory brainstem response described in the present invention can realize the functions of each module independently through the necessary hardware and software cooperation according to the actual application, or some powerful functional processing units can realize the functions of multiple modules, and the present invention is not limited thereto.

Although the contents of the present invention have been described in detail by the above preferred embodiments, it should be recognized that the above description should not be considered a limitation of the present invention. A variety of modifications and replacements to the present invention will be apparent to those skilled in the art after reading the foregoing. Accordingly, the scope of protection of the present invention shall be limited by the appended claims.

The invention claimed is:

1. An automatic test method for auditory brainstem response (ABR), comprising:
   A1, acquiring corresponding ABR recordings at an initial loudness level;
   A2, gradually increasing, based on an operation of an adaptive average method, the times of level averaging through iteration until conditions of an ABR signal detection are met;
   the conditions of the ABR signal detection including:
   after grouping ABR recordings upon a current loudness level in a current iteration, respectively
   calculating an average curve of each group according to current average times,
   obtaining a time lag where a maximum value of cross-correlation coefficient between the groups is located, and
   judging whether an ABR signal with a time-locked characteristic exists based on the rule that whether a deviation of the time lag is within a specified range;
   A3, judging whether the ABR signal is detected in step A2:
   if the ABR signal is detected, executing step A4;
   if the ABR signal is not detected, executing step A5;
   A4, judging whether the current loudness level reaches a set minimum;
   if the minimum loudness level is not reached, acquiring the ABR dataset at an updated loudness level and combining with recorded datasets, re-executing step A2, the updated loudness level being obtained by subtracting a set step size from the current loudness level;
   if the minimum loudness level is reached, executing step A6;
   A5, judging whether the ABR signal is not detected at successive P loudness levels: if the ABR signal is not detected for the successive P loudness levels, executing step A6; otherwise, jumping to step A4;

A6, using the minimum loudness level required for detecting the ABR signal as hearing threshold; or in the routines of the adaptive average method, obtaining the loudness level corresponding to the hearing threshold by function fitting and interpolation on the number of executed iterations used at each loudness level from the initial loudness level to the minimum loudness level.

2. The automatic test method for auditory brainstem response of claim 1, wherein in step A2, the operation of the adaptive average method comprises:
S1', dividing the ABR recordings that are time curves of which an input type is repeated single recording into two groups randomly and respectively calculating an average curve;
S2', calculating the cross-correlation coefficient of the two groups after being averaged respectively;
S3', obtaining the time lag where the maximum value of the cross-correlation coefficient is located;
S4', comparing an absolute value of the time lag with a value of k to judge whether a deviation of the time lag is within k data points:
if the absolute value of the time lag is less than the value of k, indicating that the deviation of the time lag is within the k data points, which denotes that a stable time-locked signal is detected, then stopping the data acquisition, which corresponds to a case that the ABR signal is detected;
if the absolute value of the time lag is not less than the value of k, indicating that the deviation of the time lag is not within the k data points, which denotes that no stable time-locked signal is detected, then proceeding to step S5';
S5', judging whether a maximum number of iterations at the current loudness level is reached;
if the maximum number of iterations is reached, stopping the data acquisition, which corresponds to the case that no ABR signal is detected; if the maximum number of iterations is not reached, further adding newly acquired ABR recordings to currently registered ABR dataset, and executing the operations of S1' to S5' repeatedly at the current loudness level;
wherein k is a preset fixed value, or a value obtained by calculating all data points according to a preset proportion.

3. The automatic test method for auditory brainstem response of claim 1, wherein in step A2, the operation of the adaptive average method comprises:
performing a parallel judgment on the ABR recordings that are time curves of which an input type is repeated single recording for Q times, executing steps S1 to S4 in each time;
S1, dividing currently registered ABR dataset into two groups randomly and calculating average curves respectively;
S2, calculating the cross-correlation function of the two groups after being averaged respectively;
S3, obtaining the time lag where the maximum value of the cross-correlation coefficient is located;
S4, comparing an absolute value of the time lag with a value of k to judge whether a deviation of the time lag is within k data points:
if the absolute value of the time lag is less than the value of k, indicating that the deviation of the time lag is within the k data points, which denotes that a stable time-locked signal is detected;
if the absolute value of the time lag is not less than the value of k, indicating that the deviation of the time lag is not within the k data points, which denotes that no stable time-locked signal is detected;
S5, judging whether the stable time-locked signal is detected each time in the parallel judgment for Q times:
if the stable time-locked signal is detected in each of the Q times, stopping the data acquisition, which corresponds to a case that the ABR signal is detected;
if the stable time-locked signal is not detected in each of the Q times, further executing step S6:
S6, judging whether a maximum number of iterations at the current loudness level is reached:
if the maximum number of iterations is reached, stopping the data acquisition, which corresponds to the case that no ABR signal is detected;
if the maximum number of iterations is not reached, further adding newly acquired ABR recordings to currently registered ABR dataset, and executing the operations of S1 to S6 repeatedly at the current loudness level;
wherein k is a preset fixed value, or a value obtained by calculating all data points according to a preset proportion.

4. The automatic test method for auditory brainstem response of claim 1, wherein in step A2, the operation of the adaptive average method comprises:
S1", the ABR dataset being a time curve of which an input type is a plurality of averaged recordings, combining the average curve $avgA_{add}$ which is newly added in a present iteration with the average curve $avgA_{old}$ of a previous iteration to obtain an updated average curve $avgA_{new}$ according to a weight calculation $$avgA_{new} = \frac{(M-1) \times avgA_{old} + avgA_{add}}{M}$$

wherein Q groups of $avgA_{new}$, $avgA_{old}$, $avgA_{add}$ are provided, respectively; M is a current number of iterations;
S2", calculating the cross-correlation function between each two groups for the current average curve $avgA_{new}$ of the Q groups;
S3", obtaining time lags of the Q groups where the maximum value of the cross-correlation coefficient is located;
S4", in the parallel judgment for Q times, comparing an absolute value of the time lag of each group with a value of k to judge whether a deviation of the time lag is within k data points: if the absolute value of the time lag is less than the value of k, indicating that the deviation of the time lag is within the k data points, which denotes that a stable time-locked signal is detected; if the absolute value of the time lag is not less than the value of k, indicating that the deviation of the time lag is not within the k data points, which denotes that no stable time-locked signal is detected;
S5", judging whether the stable time-locked signal is detected each time in the parallel judgment for Q times:
if the stable time-locked signal is detected in each of the Q times, stopping the data acquisition, which corresponds to a case that the ABR signal is detected;
if the stable time-locked signal is not detected in each of the Q times, further executing step S6":
S6", judging whether a maximum number of iterations at the current loudness level is reached;

if the maximum number of iterations is reached, stopping the data acquisition, which corresponds to the case that no ABR signal is detected; if the maximum number of iterations is not reached, further adding newly acquired ABR test average data to currently registered ABR test average data, and executing the operations of S1" to S6" repeatedly at the current loudness level;

wherein k is a preset fixed value, or a value obtained by calculating all data points according to a preset proportion.

5. The automatic test method for auditory brainstem response of claim 1, wherein the average times used in calculating the ABR recording average curve at each sound loudness level is a product of the number of iterations and a value of N;

the value of N corresponds to the number of groups of the newly added ABR recordings at each iteration.

6. The automatic test method for auditory brainstem response of claim 1, wherein in step A6, after the number of iterations used at each sound loudness level is normalized, the sound loudness level corresponding to the hearing threshold is obtained by Sigmoid function fitting and interpolation.

7. The automatic test method for auditory brainstem response of claim 1, wherein the ABR dataset at each sound loudness level are animal experimental data or clinical data, obtained through real-time testing or stored offline; and the ABR dataset are preprocessed by one or more of:
  signal amplification;
  bandpass filtering;
  adjusting a time interval of ABR waveform acquisition, selecting an ABR time curve in a corresponding time interval after sound stimulation is started as an object of analysis;
  excluding an ABR time curve corresponding to background noise; and
  removing low-frequency background noise by means of a smooth spline fitting function.

8. An automatic test device for auditory brainstem response which is applied to the automatic test method for auditory brainstem response of claim 1, wherein the automatic test device for auditory brainstem response comprises:
  an input module that acquires ABR dataset acquired at a stimulation of each sound loudness level;
  a control module that drives the input module to acquire ABR dataset acquired in batches at the stimulation of each sound loudness level from an initial loudness level to a minimum loudness level;
  an adaptive average method operation module that executes an operation of an adaptive average method to gradually increase the times of level averaging through iteration until conditions of ABR signal detection are met; the conditions of the ABR signal detection including: after grouping ABR dataset upon a current loudness level in a current iteration, respectively calculating an average curve of each group according to current average times, obtaining a time lag where a maximum value of cross-correlation coefficient between the groups is located, and judging whether an ABR signal with a time-locked characteristic exists based on the rule that whether a deviation of the time lag is within a specified data point range;
  a storage module that stores the number of iterations used at each sound loudness level during the operation of the adaptive average method; and
  a main judgment module that judges whether the ABR signal is detected during the operation of the adaptive average method according to results output by the adaptive average method operation module, when it is judged that the ABR signal is detected, further judges whether the current loudness level reaches a set minimum; or when it is judged that the ABR signal is not detected, further judges whether the ABR signal is not detected for P consecutive sound loudness levels;
  wherein if it is judged that the minimum loudness level is not reached, the main judgment module issues an instruction to the control module, and the control module further drives the input module to acquire the ABR dataset at an updated loudness level; the updated loudness level is obtained by subtracting the step size from the current loudness level;
  or, if it is judged that the minimum loudness level is reached, the main judgment module issues an instruction to the control module, and the control module calls the number of iterations used in the adaptive average operation from the storage module;
  and the lowest loudness level required to detect the ABR signal is taken as the hearing threshold.

9. The automatic test device for auditory brainstem response of claim 8, wherein the automatic test device for auditory brainstem response further comprises a function fitting module, which obtains the sound loudness level corresponding to the hearing threshold by the function fitting and interpolation on the number of executed iterations in the routines of the adaptive average method.

10. The automatic test device for auditory brainstem response of claim 8, wherein
  the adaptive average method operation module issues an instruction for collecting data to the control module,
  when a data type input by the input module is repeated single sweeps, the adaptive average method operation module executes one judgment or a plurality of parallel judgments corresponding to each iteration of each sound loudness level;
  in the one judgment or each judgment of the parallel judgments, currently registered ABR dataset are randomly divided into two groups to calculate an average curve of each group, then a time lag corresponding to the maximum value of the cross-correlation coefficient is calculated,
  an absolute value of the time lag is compared with a value of k to judge whether a deviation of the time lag is within k data points;
  if the absolute value of the time lag is less than the value of k, it denotes that a stable time-locked signal is detected;
  if the absolute value of the time lag is not less than the value of k, it denotes that no stable lock signal is detected;
  if the stable time-locked signal is detected at the current loudness level in the one judgment or each judgment of the parallel judgments, the adaptive average method operation module issues an instruction to stop data acquisition to the control module, gives return information indicating that the ABR signal is detected at the current loudness level, and stores the current number of iterations through the storage module;
  if no stable time-locked signal is detected at the current loudness level in the one judgment, or if the stable time-locked signal is not detected at the current loudness level in each judgment of the parallel judgments, the adaptive average method operation module further judges whether the maximum number of iterations at the current loudness level are reached:
if the maximum number of iterations is reached, the adaptive average method operation module issues the instruction to stop data acquisition to the control module, gives return information indicating that the ABR signal cannot be detected at the current loudness level, and stores the current number of iterations through the storage module; and
if the maximum number of iterations is not reached, the adaptive average method operation module further issues an instruction to add new data to the control module, and after adding newly acquired data into original datasets, the operations of the adaptive average method are repeatedly executed at the current loudness level;
wherein k is a preset fixed value, or a value obtained by calculating all data points according to a preset proportion.

11. The automatic test device for auditory brainstem response of claim 8, wherein the adaptive average method operation module issues an instruction for collecting data to the control module,
when a data type input by the input module is a plurality of average dataset, the adaptive average method operation module combines the average curve $avgA_{add}$ which is newly added in a present iteration with the average curve $avgA_{old}$ of a previous iteration to obtain an updated average curve $avgA_{new}$ according to a weight calculation $$avgA_{new} = \frac{(M-1) \times avgA_{old} + avgA_{add}}{M}$$

wherein $avgA_{new}$, $avgA_{old}$, $avgA_{add}$ are average data of ABR test of Q group;
M is a current number of iterations;
the adaptive average method operation module calculates the cross-correlation function between each two groups for the updated average curve $avgA_{new}$ of the Q groups, and obtained time lags of the Q groups where the maximum value of the cross-correlation coefficient is located;

in the parallel judgment for Q times, an absolute value of the time lag of each group is compared with a value of k to judge whether a deviation of the time lag is within k data points:
if the absolute value of the time lag is less than the value of k, it indicates that the deviation of the time lag is within the k data points, which denotes that a stable time-locked signal is detected;
if the absolute value of the time lag is not less than the value of k, it indicates that the deviation of the time lag is not within the k data points, which denotes that no stable time-locked signal is detected;
the adaptive average method operation module judges whether the stable time-locked signal is detected each time in the parallel judgment for Q times:
if the stable time-locked signal is detected in each of the Q times, the adaptive average method operation module issues an instruction to stop data acquisition to the control module, gives return information indicating that the ABR signal is detected at the current loudness level, and stores the current number of iterations through the storage module;
if the stable time-locked signal is not detected in each of the Q times, the adaptive average method operation module further judges whether the maximum number of iterations is reached:
if the maximum number of iterations is reached, the adaptive average method operation module issues the instruction to stop data acquisition to the control module, gives return information indicating that the ABR signal is detected at the current loudness level, and stores the current number of iterations through the storage module; and
if the maximum number of iterations is not reached, the adaptive average method operation module further adds newly acquired ABR test data to currently registered ABR test average data, and executes the operations of the adaptive average method repeatedly at the current loudness level;
wherein k is a preset fixed value, or a value obtained by calculating all data points according to a preset proportion.

* * * * *